(12) United States Patent
Bove et al.

(10) Patent No.: US 6,846,379 B1
(45) Date of Patent: Jan. 25, 2005

(54) FLEXIBLE MAGNETIC INSOLE AND METHOD OF MANUFACTURE

(75) Inventors: Anthony Bove, Port Jefferson, NY (US); Vincent Ardizzone, Miller Place, NY (US)

(73) Assignee: Nu-magnetics, Inc., Port Jefferson, NY (US)

( * ) Notice: Subject to any disclaimer, the term of this patent is extended or adjusted under 35 U.S.C. 154(b) by 257 days.

(21) Appl. No.: 10/004,143

(22) Filed: Oct. 23, 2001

Related U.S. Application Data

(62) Division of application No. 09/379,826, filed on Aug. 23, 1999, now Pat. No. 6,322,491, which is a continuation-in-part of application No. 09/038,508, filed on Mar. 10, 1998, now abandoned, which is a continuation-in-part of application No. 08/911,950, filed on Aug. 15, 1997, now Pat. No. 6,293,900, which is a continuation-in-part of application No. 08/678,348, filed on Jul. 11, 1996, now Pat. No. 5,871,438, which is a continuation of application No. 08/573,390, filed on Dec. 15, 1995, now Pat. No. 5,538,495, which is a continuation-in-part of application No. 08/565,826, filed on Dec. 1, 1995, now abandoned, which is a continuation of application No. 08/427,733, filed on Apr. 24, 1995, now Pat. No. 5,514,072, which is a continuation of application No. 08/276,876, filed on Jul. 18, 1994, now abandoned, which is a continuation of application No. 08/158,607, filed on Nov. 29, 1993, now abandoned, which is a continuation of application No. 07/990,927, filed on Dec. 14, 1992, now Pat. No. 5,277,692, which is a continuation of application No. 07/823,149, filed on Jan. 21, 1992, now abandoned.

(60) Provisional application No. 60/118,832, filed on Feb. 5, 1999.

(51) Int. Cl.$^7$ ............................................. B32B 31/00
(52) U.S. Cl. ........................ 156/272.4; 156/253; 36/44
(58) Field of Search .............................. 156/252, 253, 156/272.4; 600/9, 15; 36/43, 44; 335/284

(56) References Cited

U.S. PATENT DOCUMENTS

| | | | |
|---|---|---|---|
| 3,127,544 A | * 3/1964 | Blume | 335/284 |
| 4,240,437 A | 12/1980 | Church | 128/420 R |
| 4,401,961 A | 8/1983 | Baermann et al. | 335/285 |
| 4,489,711 A | 12/1984 | Latzke | 128/1.3 |
| 4,549,532 A | * 10/1985 | Baermann | 600/15 |
| 4,550,714 A | 11/1985 | Talish et al. | 128/1.5 |
| 4,587,956 A | 5/1986 | Griffin et al. | 128/1.3 |
| 4,633,598 A | * 1/1987 | Moronaga et al. | 36/44 |
| 4,731,297 A | 3/1988 | Takaya | 428/553 |

(List continued on next page.)

*Primary Examiner*—Blaine Copenheaver
*Assistant Examiner*—John L. Goff
(74) *Attorney, Agent, or Firm*—Cislo & Thomas LLP

(57) ABSTRACT

A magnetic insole provides cushioned magnetotherapy for the soles of a wearer's feet. A laminated insole in the general shape of a foot is inserted into a shoe to provide magnetotherapy to the wearer's foot adjacent the sole. Collateral therapeutic effects may be effected as such magnetotherapy may affect the nerve endings in the foot and collateral, corresponding, or related tissue structures in the body. A flexible magnetic core provides alternating magnetic fields in a regular pattern thereby to provide magnetotherapy to the foot. A cushioning base acts as an underpad for the magnetic insole in order to provide greater comfort and cushioning for the user's foot. The flexible magnetic core is constructed by mixing strontium ferrite, barium ferrite, or other strongly ferromagnetic material and with an elastic binder such as neoprene.

17 Claims, 8 Drawing Sheets

U.S. PATENT DOCUMENTS

| | | | | |
|---|---|---|---|---|
| 4,798,194 A | | 1/1989 | Amishima | 128/9 |
| 4,843,738 A | * | 7/1989 | Masuda | 36/44 |
| 5,017,185 A | | 5/1991 | Baermann | 600/15 |
| 5,045,050 A | | 9/1991 | Liboff et al. | 600/9 |
| 5,067,940 A | | 11/1991 | Liboff et al. | 600/13 |
| 5,084,003 A | | 1/1992 | Susic | 600/13 |
| 5,085,626 A | | 2/1992 | Frey | 600/13 |
| 5,092,835 A | | 3/1992 | Schurig et al. | 600/9 |
| 5,195,941 A | | 3/1993 | Erickson et al. | 600/14 |
| 5,226,020 A | | 7/1993 | Li et al. | 368/10 |
| 5,226,185 A | | 7/1993 | Guay et al. | 5/448 |
| 5,266,914 A | | 11/1993 | Dickson et al. | 335/288 |
| 5,267,939 A | | 12/1993 | Liboff et al. | 600/13 |
| 5,277,692 A | | 1/1994 | Ardizzone | 600/9 |
| 5,295,494 A | | 3/1994 | Rodriguez | 128/845 |
| 5,304,111 A | | 4/1994 | Mitsuno et al. | 600/9 |
| 5,312,321 A | | 5/1994 | Holcomb | 600/9 |
| 5,314,401 A | | 5/1994 | Tepper | 600/14 |
| 5,389,061 A | | 2/1995 | Nor | 600/15 |
| 5,426,925 A | | 6/1995 | Smargiassi | 54/79.1 |
| 5,450,858 A | | 9/1995 | Zablotsky et al. | 128/876 |
| 5,453,073 A | | 9/1995 | Markoll | 600/14 |
| 5,459,445 A | | 10/1995 | Je | 335/214 |
| 5,478,303 A | | 12/1995 | Foley-Nolan et al. | 600/15 |
| 5,514,072 A | | 5/1996 | Ardizzone | 600/9 |
| 5,632,720 A | | 5/1997 | Kleitz | 601/15 |
| 5,642,739 A | | 7/1997 | Fareed | 128/881 |
| 5,665,049 A | | 9/1997 | Markoll | 600/14 |
| 5,700,234 A | | 12/1997 | Masuda | 600/15 |
| 5,707,333 A | | 1/1998 | Bakst | 600/9 |
| 5,709,223 A | | 1/1998 | Rawls, Jr. et al. | 128/898 |
| 5,714,927 A | | 2/1998 | Henderson et al. | 340/435 |
| 5,728,058 A | | 3/1998 | Ouellette et al. | 602/62 |
| 5,738,624 A | | 4/1998 | Zablotsky et al. | 600/9 |
| 5,766,236 A | | 6/1998 | Detty et al. | 607/149 |
| 5,782,743 A | | 7/1998 | Russell | 600/9 |
| 5,871,438 A | * | 2/1999 | Ardizzone | 600/9 |

* cited by examiner

FIG. 2

```
┌─────────────────────────────────────┐
│  CREATE AND PREPARE LAMINATED       │
│  SHEET OF LEATHER UPPER, FLEXIBLE   │
│  MAGNETIC CORE, AND CUSHIONING      │
│              BASE                   │
│                                  70 │
└─────────────────────────────────────┘
                  │
┌─────────────────────────────────────┐
│   CUT INSOLE SECTION PAIRS FROM     │
│           LAMINATE SHEET            │
│                                  72 │
└─────────────────────────────────────┘
                  │
┌─────────────────────────────────────┐
│       PERFORATE INSOLE SECTIONS     │
│                                  74 │
└─────────────────────────────────────┘
```

FIG. 3

| PREPARE MIXTURE BY MIXING ON TWO-ROLL MILL | 80 |

| PREPARE PIGS FROM ROLLED MATERIAL | 82 |

| CALENDAR PIGS TO CREATE SHEET | 84 |

| APPLY NYLON MESH | 86 |

| MAGNETIZE | 88 |

| FORM INTO LAMINATE WITH UPPER AND BASE | 90 |

|   |   |   |   |   |
|---|---|---|---|---|
| N | S | N | S | N |
| S | N | S | N | S |
| N | S | N | S | N |
| S | N | S | N | S |
| N | S | N | S | N |

FIG. 5

FLEXIBLE MAGNETIC INSOLE AND METHOD OF MANUFACTURE

CROSS-REFERENCES TO RELATED APPLICATIONS

This application is related to U.S. provisional patent application Ser. No. 60/118,832 filed Feb. 5, 1999 for a Magnetic Insole and Method of Manufacture.

This application is a continuation-in-part application of U.S. patent application Ser. No. 09/038,508 filed Mar. 10, 1998, for a Magnetic Wrap for Joints;

which is a continuation-in-part of U.S. patent application Ser. No. 08/911,950 filed Aug. 15, 1997, for a Magnetic Face Mask, now U.S. Pat. No. 6,293,900 issued Sep. 25, 2001;

which is a continuation-in-part application of U.S. patent application Ser. No. 08/678,348 filed Jul. 11, 1996, for a Flexible Magnetic Pad With Multi-Directional Constantly Alternating Polarity Zones, now U.S. Pat. No. 5,871,438 issued Feb. 16, 1999;

which is a continuation of application Ser. No. 08/573,390, filed Dec. 15, 1995, for a Flexible Magnetic Pad With Multi-Directional Constantly Alternating Polarity Zones, now U.S. Pat. No. 5,538,495 issued Jul. 23, 1996, which is a continuation of application Ser. No. 08/427,733, filed Apr. 24, 1995, for a Flexible Magnetic Pad With Multi-Directional Constantly Alternating Polarity Zones, now U.S. Pat. No. 5,514,072 issued May 7, 1996;

which is a continuation of application Ser. No. 08/276,876, filed Jul. 18, 1994, now abandoned; which is a continuation of application Ser. No. 08/158,607, filed Nov. 29, 1993, now abandoned;

which is a continuation of application Ser. No. 07/990,927, filed Dec. 14, 1992, for a Flexible Magnetic Pad With Multi-Directional Constantly Alternating Polarity Zones, now U.S. Pat. No. 5,277,692 issued Jan. 11, 1994;

which is a continuation of application Ser. No. 07/823,149, filed Jan. 21, 1992, now abandoned.

This application is a divisional application of U.S. patent application Ser. No. 09/379,826 filed Aug. 23, 1999, for a Flexible Magnetic Insole and Method of Manufacture, now U.S. Pat. No. 6,322,491 issued Nov. 27, 2001; which is a continuation-in-part of U.S. patent application Ser. No. 08/565,826 filed Dec. 1, 1995, now abandoned.

The contents of all applications of which the present application is a divisional, continuation, continuation-in-part, or otherwise from which this application is related are incorporated herein by this reference thereto.

BACKGROUND OF THE INVENTION

1. Field of the Invention

This invention relates to magnetotherapeutic devices, and more particularly to a magnetotherapeutic insole for a shoe or the like and a method for manufacturing a flexible magnetic core for the same.

2. Description of the Related Art

Magnetotherapy uses magnetic fields to provide therapeutic and restorative treatment to limbs, organs, and other parts of the body. Generally, one means by which magnetotherapy may be achieved is by bringing a magnet or a series of magnets into close proximity to the affected body part or organ of interest. As is known according to Faraday's Law of Magnetic Induction, as well as the Hall Effect, charged particles experience a force acting on them when they move through a magnetic field in a perpendicular direction. Since human blood is replete with ions and electrolytes, it has many charged molecules, particles, and the like which experience a force, including an aligning force, when moving through a magnetic field. When exposed and caused to so travel through a magnetic field, such ions and electrolytes may generate heat, causing the associated blood vessel to widen. The widening of the blood vessel would then allow increased volumes of blood to flow through the blood vessel.

Polar molecules (such as water) also respond to magnetic fields in a manner similar to that for charged molecules. Additional therapeutic or restorative effects might arise through the alignment of polar molecules as they pass through the magnetic field. When subject to a magnetic field, polar molecules rotate to align themselves with the field. Such alignment would alternate with the magnetic polarity as the polar molecules traveled through different regions of such magnetic polarity. The mechanical motion of the rotation of such polar molecules might also cause heating and the like and would also stimulate, mix, or agitate the blood in a gentle manner, causing it to gently churn. Such mixing of the blood at the molecular level may cause it to more easily recognize foreign matter. By recognizing foreign matter, the blood and/or immune system may be able to more readily address such foreign matter.

Several patents are known having various designs for the alternation of magnets of different polarity to provide spatially diverse magnetic fields. The patent to Latzke (U.S. Pat. No. 4,489,711 issued Dec. 25, 1984) and the patents to Ardizzone (U.S. Pat. No. 5,277,692 issued Jan. 11, 1994; U.S. Pat. No. 5,514,072 issued May 7, 1996; and U.S. Pat. No. 5,538,495 issued Jul. 23, 1996) all disclose a variety of magnetic plaster and magnetic pads having certain magnetic geometries in order to achieve spatially varying magnetic fields through the use of magnets.

In the past, the only way to offer or provide both mechanical support and magnetic therapy was to insert magnets between a brace and the associated body joint. Recently, stronger static magnetic materials have become more readily available in the commercial market. Particularly, permanent magnets incorporating the element neodymium (atomic number 60) provide strong magnetic fields at common temperatures (below 120° F./50° C.). Strontium ferrite also provides a useful magnetic substrate. Barium ferrite also exhibits characteristics useful for a magnetic substrate. Such magnets can be incorporated into flexible fabrics or the like to provide a flexible material suitable for wrapping around joints.

By using flexible and/or elastic materials such as neoprene, nitrile, or SBR, a magnetotherapeutic foot insole previously unseen in the art could be realized. While certain portions of the human body have been emphasized as being subject to the use of magnetotherapeutic devices, it remains to be seen in the art to provide such magnetotherapy in the form of an insole to be worn within shoes or other footwear.

The sole of the foot is known for its sensitivity and for the fact that several nerve endings terminate in the sole of the foot. In some schools of medicinal thought, the sole of the foot provides therapeutic access to other parts of the body due to the connection of the nerves in the foot with such other areas. For example, in Chinese and other Oriental forms of medicine, different areas of the foot may correspond to different areas of the body. Affecting one part of the sole of a person's foot thereby may: influence the biological or biochemical activities in other areas of the body. As is known with acupuncture, the stimulation or engagement of nerves, plexus, or the like by long, thin needles may serve to affect other areas of the body. The same may be similarly true with magnetotherapeutic devices when applied to various areas.

Consequently, the art has yet to address ongoing magnetotherapy for the foot, particularly the sole of the foot, which may provide therapeutically advantageous effects not only to the foot area itself, but to the corresponding or collateral areas affected by the nerves or other tissues associated with the sole of the foot.

SUMMARY OF THE INVENTION

The magnetic insole of the present invention provides cushioned magnetotherapy for the soles of a wearer's feet. A laminated insole in the general shape of a foot is inserted into a shoe to provide magnetotherapy to the wearer's foot adjacent the sole. Collateral therapeutic effects may be effected as such magnetotherapy may affect the nerve endings in the foot and collateral, corresponding, or related tissue structures in the body. A leather upper is used to bear the abrasion between the foot and the magnetic insole. A flexible magnetic core provides alternating magnetic fields in a regular pattern thereby to provide magnetotherapy to the foot. A cushioning base acts as an underpad for the magnetic insole in order to provide greater comfort and cushioning for the user's foot.

The flexible magnetic core is constructed by mixing strontium ferrite, barium ferrite, or other strongly ferromagnetic material and with an elastic binder such as neoprene. Additional minor constituents are also added to aid processing. The ferromagnetic material-elastic mixture is mixed together on a two (2) roll rubber mill as is known in the art, pigged, calendared, magnetized, and cut to size. The resulting sheet may then be laminated on its top side by leather upper material and on the bottom side by cushioning material so as to provide a three (3) layer laminated sheet from which magnetic: insoles of the present invention may be cut and perforated.

The magnetic insole corresponds to the inside of the shoe or other footwear. The magnetic insole is perforated to allow ventilation and airflow through the magnetic insole. The insole is generally comfortable, providing cushioning and durability, as well as providing magnetotherapy to the underside, or sole, of the person's foot.

The magnetic insole of the present invention is provided by a flexible and highly magnetic core that is sandwiched between a cushioning bottom or base layer and a leather upper. The flexible magnetic core uses strongly magnetic material, such as strontium or barium ferrite, to provide a substrate for the permanent installation of a strong magnetic field.

Proprietary magnetic field arrangements may be invested in the magnetic core portion of the magnetic insole.

Upon fabrication of the magnetic insole of the, present invention, the insole is inserted into the shoe or other footwear so that it lies flat upon the last of the shoe. The user's foot then is inserted into the shoe atop the magnetic insole which applies magnetotherapy to the user's foot so long as the user wears the shoe with the magnetic insole.

OBJECTS OF THE INVENTION

It is an object of the present invention to provide a magnetic insole.

It is yet another object of the present invention to provide a magnetic core for a magnetic insole.

It is another object of the present invention to provide a flexible magnetic core for a magnetic insole.

It is another object of the present invention to provide a method by which a flexible magnetic core can be fabricated for a magnetic insole.

It is yet another object of the present invention to provide a cushioned, flexible, and comfortable magnetic insole that allows ventilating airflow through itself.

These and other objects and advantages of the present invention will be apparent from a review of the following specification and accompanying drawings.

BRIEF DESCRIPTION OF THE DRAWINGS

FIG. 2 is a step diagram of the overall method used to create the flexible magnetic insole shown in FIG. 1.

FIG. 3 is a stepwise diagram showing the steps used to create the flexible magnetic core leading up to the flexible magnetic insole of FIG. 1.

Figure 5:
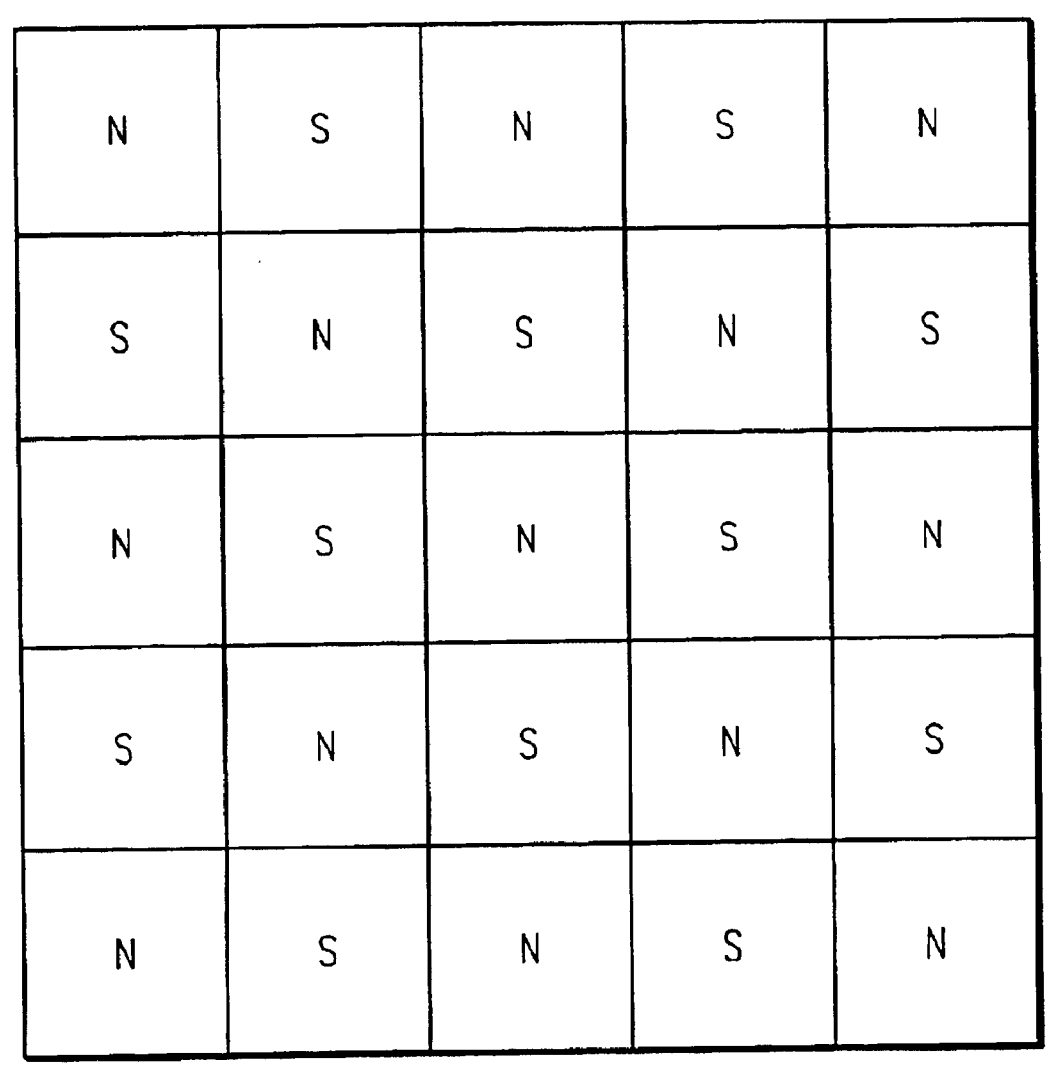

FIG. 5 is an alternating magnetic checkerboard pattern similar to that shown in FIG. 4 that may be used in the flexible magnetic insole of FIG. 1.

DESCRIPTION OF THE PREFERRED EMBODIMENT(S)

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
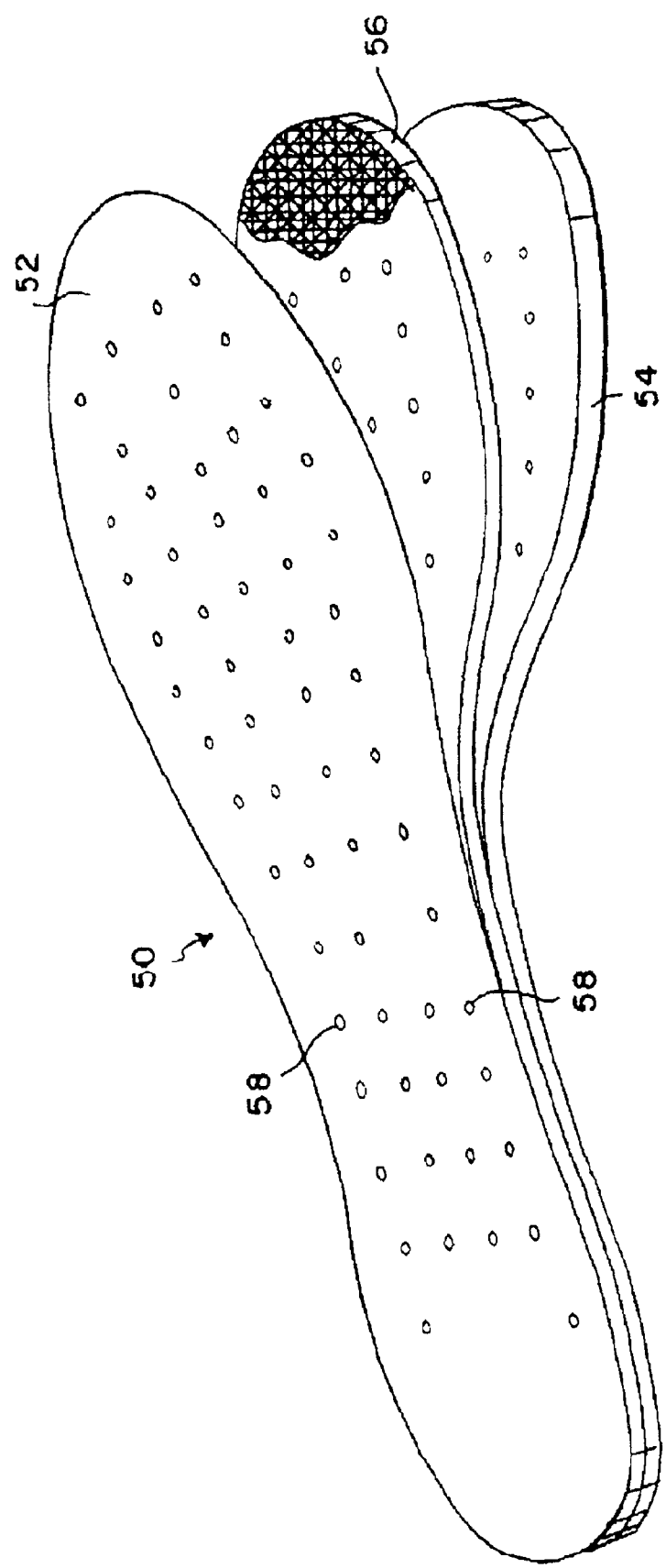
FIG. 1 shows a right perspective view of a right magnetic insole of the present invention. The front end of the magnetic insole is partially delaminated to show the layers. A partial cutaway view of the middle magnetic layer shows alternating magnetic polarity.
Figure 4:
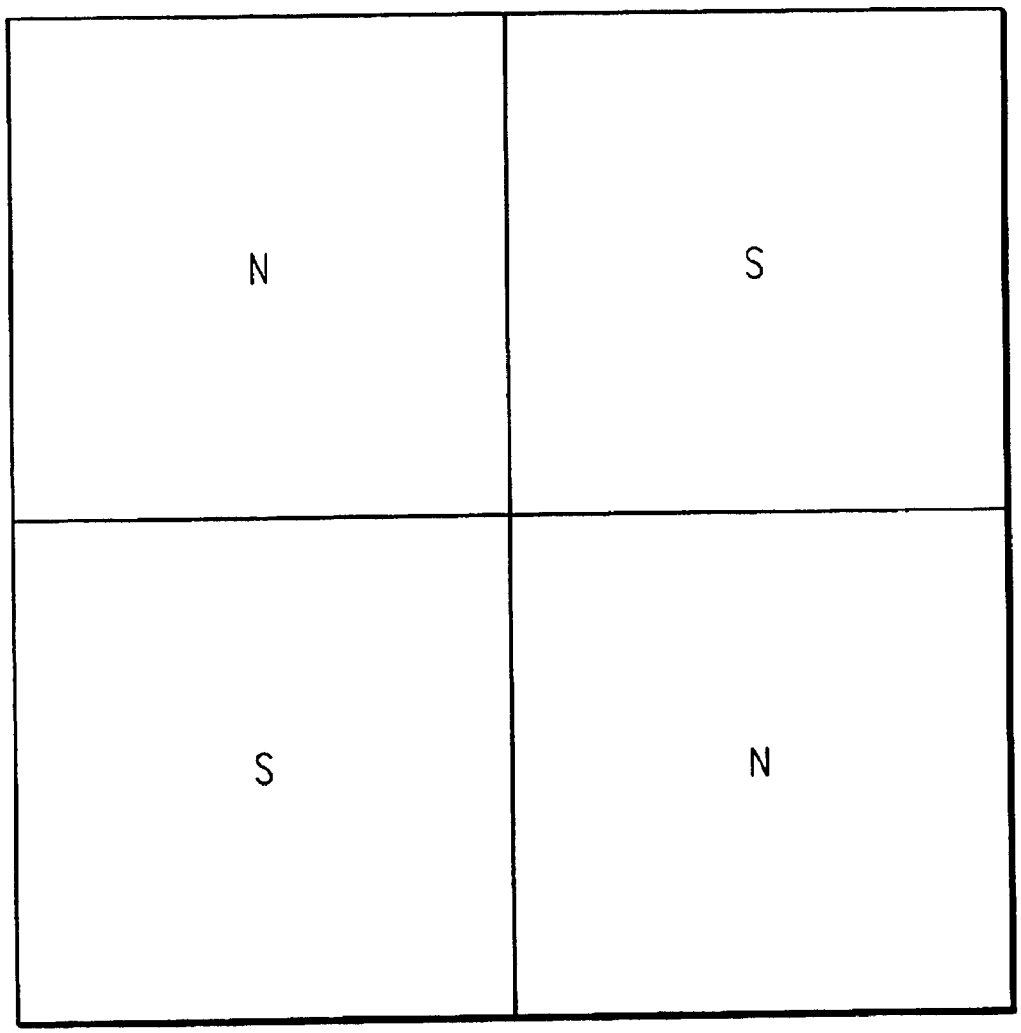
FIG. 4 shows a basic checkerboard configuration of alternating magnetic regions as used in the magnetic insole shown in FIG. 1.
Figure 6:
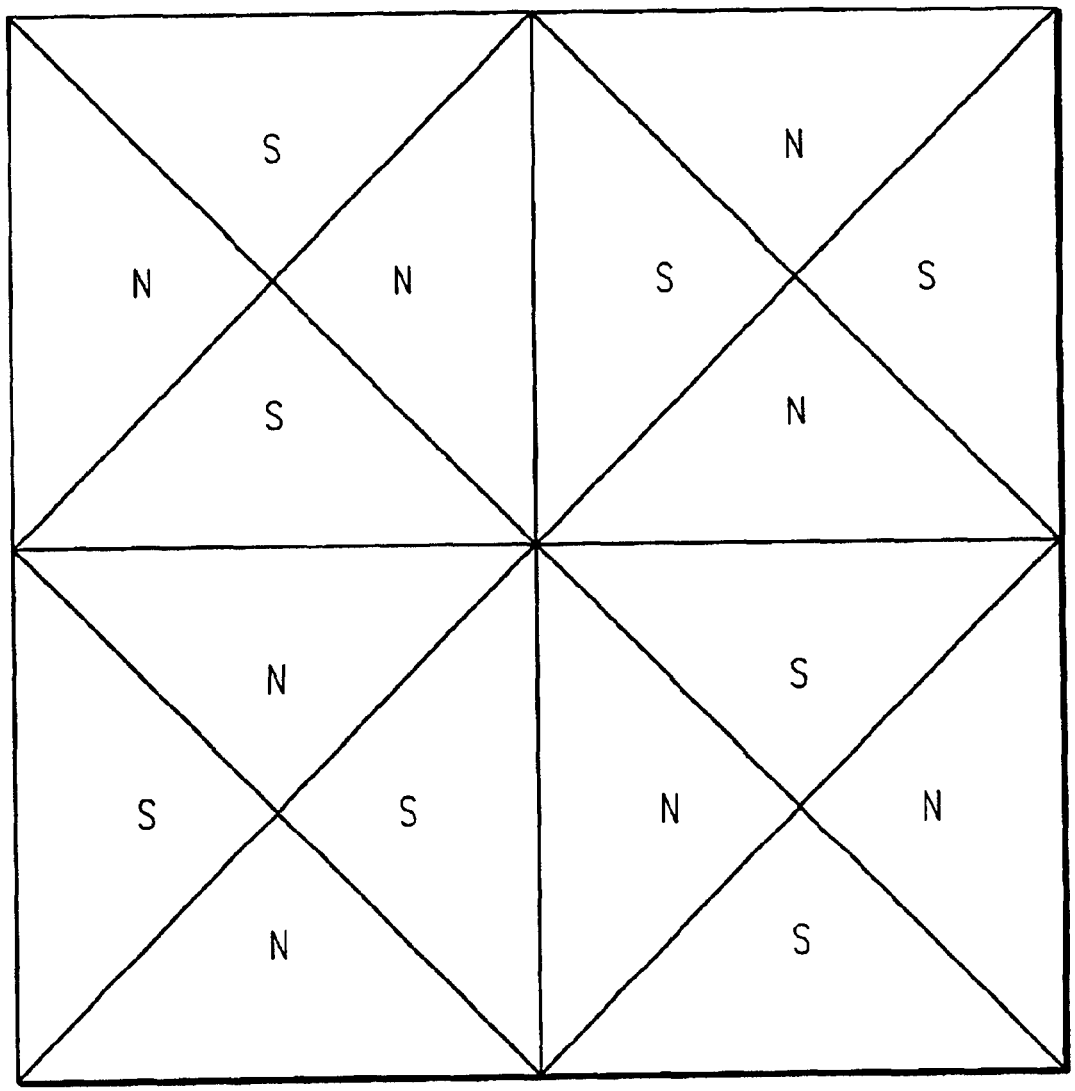
FIGS. 6 and 7 show alternating triangular checkerboard patterns that may be used in the flexible magnetic insole of FIG. 1.
Figure 7:
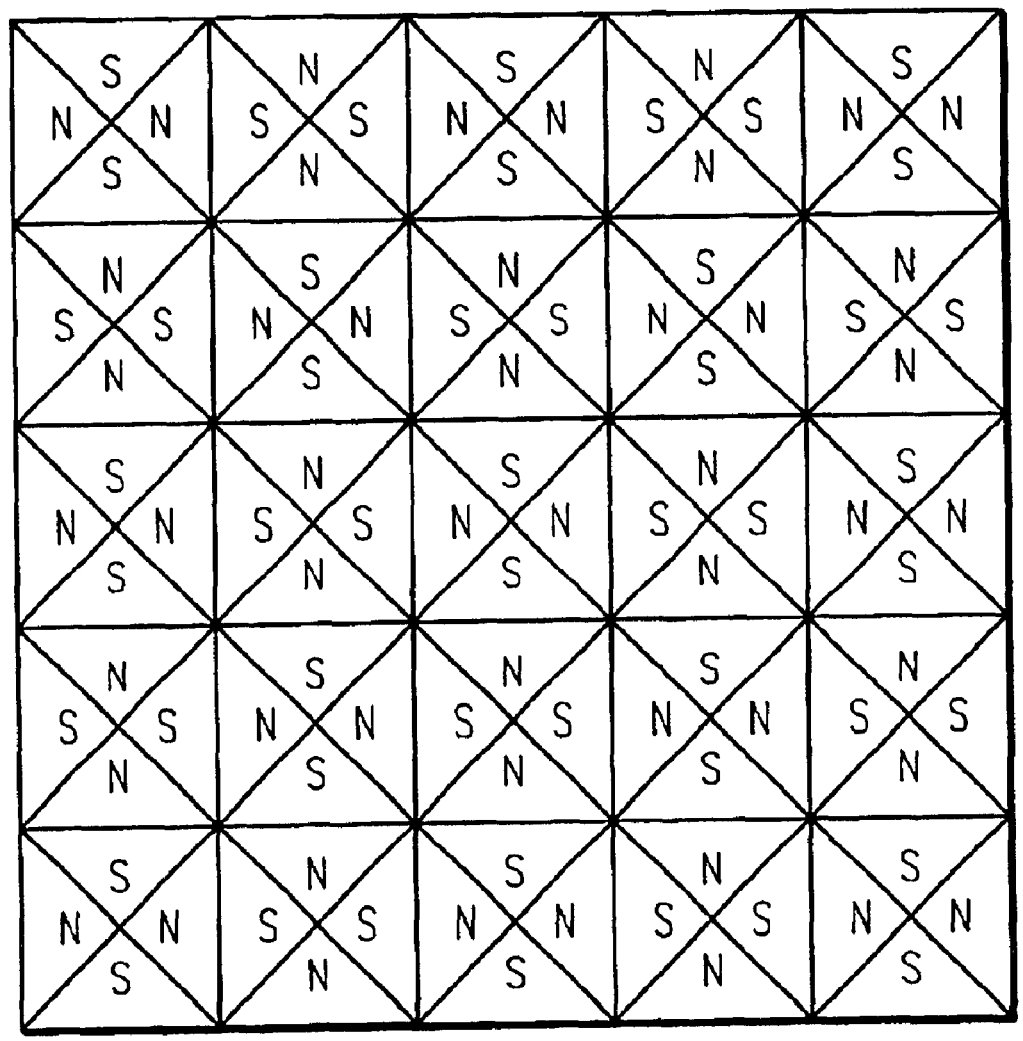
Figure 8:
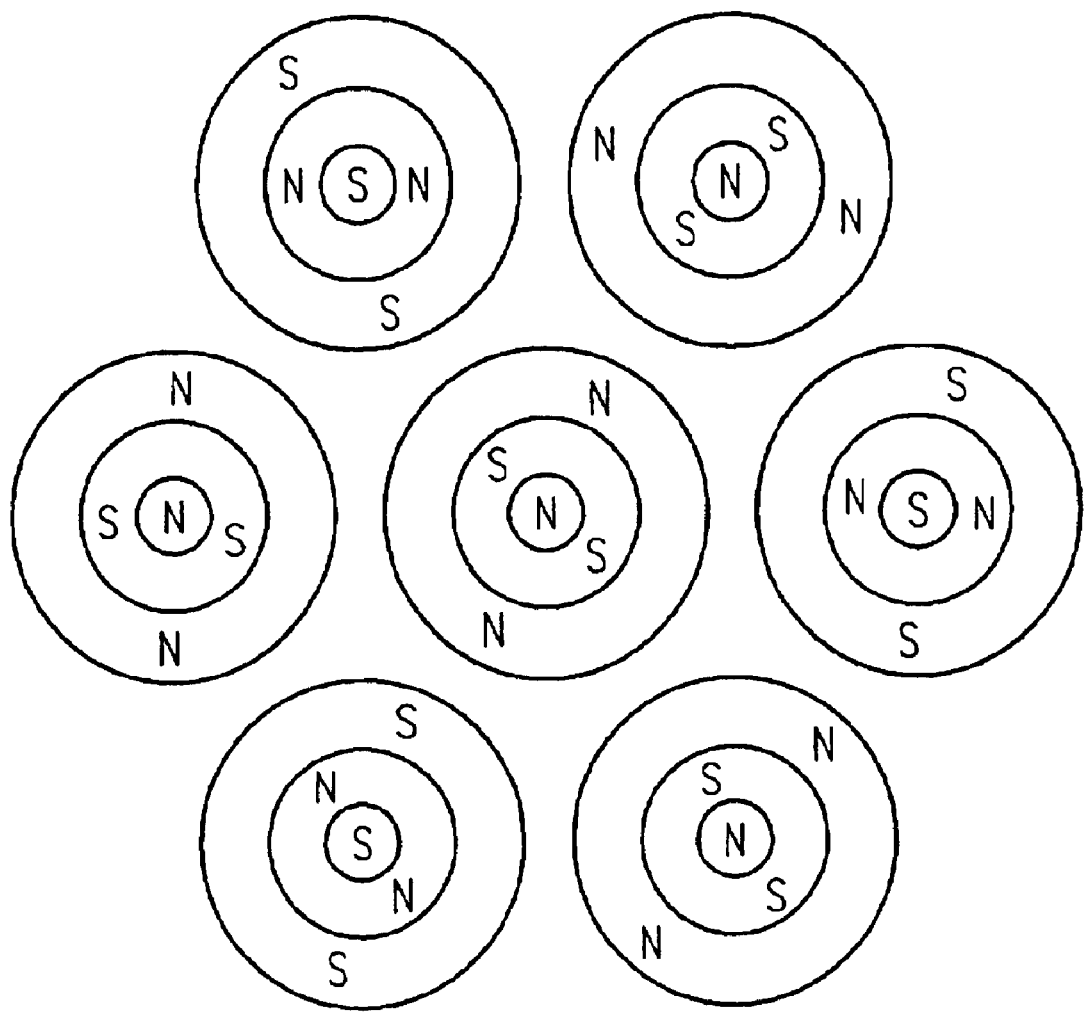
FIG. 8 shows a circular and toroidal alternating polarity magnetic field configuration that may be used in the flexible magnetic insole of FIG. 1.

As shown in FIG. 1, the flexible magnetic insole 50 of the present invention has a leather upper 52 and a cushioning base 54. A flexible magnetic core 56 is sandwiched between the leather upper 52 and the cushioning base 54.

The leather upper 52 is meant to provide a comfortable and resilient contact surface between the magnetic insole 50 of the present invention and the wearer's foot. Leather is seen as being a most advantageous material to use as it is durable, comfortable, and malleable in order to conform to the specific geometries of the wearer's foot. Other mater ials having these qualities may also be put to good use, including synthetic materials resembling and wearing like leather. As used herein, the term "leather" indicates all such material usable as leather for the leather upper 52.

The cushioning base 54 may be made of Sorbothane® padding or other similar padding as is available in the art. A durable substance capable of withstanding the in-shoe environment is preferable so as to provide good use and wear to the wearer.

As can be seen from FIG. 1, the magnetic insole 50 of the present invention may be approximately one to two-tenths inch (1/10"–2/10") high and shaped to conform to the inside of a shoe. The magnetic insole 50 of the present invention is intended to fit inside the shoe just above the sock liner or other material that would otherwise form the layer of the shoe immediately beneath the sock or foot of the wearer.

As can be seen in FIG. 1, the magnetic insole 50 has a series of perforations 58 that pass through the magnetic insole 50. These perforations 58 serve to allow air to pass through the magnetic insole 50 so that it may ventilate both itself and the underlying portions of the shoe.

To construct the magnetic insole 50 of the present invention, FIG. 2 shows the basic steps by which the magnetic insole 50 is prepared. In FIG. 2, an initial creation and preparation step 70 is present whereby the individual laminate layers are prepared. A sheet of leather forming the leather upper 52 is provided or selected as is a sheet of flexible magnetic core material and cushioning base material. The sheets are laminated together 70 in order to provide an integrated laminated sheet with the three (3) magnetic insole layers.

Insole sections are then cut 72 from the laminate sheet in order to provide the initial blanks from which the ultimate magnetic insoles 50 will be prepared. As might be assumed, generally the insole sections are cut in pairs for left and right feet, although individual ones of the magnetic insoles for either the left or right foot may be cut separately.

Once an insole pair or single has been made, it is perforated 74 in order to provide the finished product.

In order to provide the flexible magnetic core 56, a very strongly magnetizable material is used in conjunction with a rubber or elastic binder, such as neoprene, nitrile, or SBR. Experience in the craft has developed, indicating that barium or strontium ferrite is one ferromagnetic material that may advantageously be used in the magnetic insole 50 of the present invention.

Approximately eighty-six percent (86%) magnetic ferrite is combined with thirteen percent (13%) elastic binder. The elastic binder serves to make flexible the resulting sheet of magnetic ferrite. Additional ingredients include stearic acid and a mold-release agent such as MoldWiz®. (MoldWiz® is known in the art as manufactured by Axel Plastics Research Laboratories, Inc. Of particular use is that mixture of Mold-Wiz® known in the trade as INT-21G. These additional ingredients provide lubricant for the individual molecular chains). Zinc oxide may be added to provide cross-linking so as to better hold together the magnetic ferrite elastomer mixture, which then sets due to cross-binding and curing.

As is set forth in the parent application for the present invention, namely Magnetic Wrap for Joints (indicated in the Cross-References to Related Applications section, above as U.S. Pat. Application Ser. No. 09/038,508 filed Mar. 10, 1998), a two (2) roll rubber mill is used to mix together the magnetic ferrite with the elastic binder. This is shown in FIG. 3 as step 80.

Using a two-roll rubber mill as is known in the art, a slower roller is coated with elastic neoprene while the entire roller structure is maintained in a cool condition as by a ten-ton chiller. The rollers may be approximately twenty inches (20") in diameter and sixty inches (60") in length. Once neoprene has fully coated: the slower roller, the magnetic ferrite (strontium ferrite) or other strongly magnetic material may be fed into the highly viscous neoprene.

The magnetic ferrite and other materials are mixed into the highly viscous neoprene to during the rolling process as it is fed into the nip, or bank, formed between the upper and faster spinning roller and the lower and slower turning roller. In addition to the magnetic ferrite or other strongly magnetic material, stearic acid, a complex fatty acid such as that known currently in the trade as INT-21G (marketed as a member of the MoldWiz® line of internal lubricants and mold releases) as manufactured by Axel Plastics Research Laboratories, of Woodside, N.Y., and zinc oxide curatives may be mixed in. These substances may form the remainder of the materials used to form the flexible magnetic core.

In mixing the filler into the rolling neoprene, it is important to ensure that the INT-21G is not mixed in prematurely as it has a tendency to increase the viscosity of the rolling neoprene beyond that which is effective for working. Consequently, it is better to work in the magnetic ferrite first before adding too much of the INT-21G. One means by which this can be effected is by loading the feeder with the magnetic ferrite and then on top of the magnetic ferrite, adding the INT-21G, possibly with the stearic acid and zinc oxide curatives.

Once the mixture has been completely rolled and processed, portions of the rolled material, known as "pigs" in the art, are prepared from the roll. This is shown as step 82 in FIG. 3. When the neoprene is worked into a sufficiently mixed condition, the rollers are stopped. "Pigs" are pulled off in strips and rolled up into a chilled calendar for pre-forming prior to pressing. Each pig is calendared into a sheet of approximately $50/1000$ of an inch by rolling it between two (2) rollers. During this pressing and rolling process, the material is heated at a temperature of over three hundred degrees Fahrenheit (300° F.) in order to provide for cross-linking and curing of the material.

Vulcanization occurs during the pressing process which may occur at approximately two hundred (200) tons pressure and 350° F. It should be noted that some forms of neoprene contain antioxidizing agents and the like to prevent oxidation of the magnetic ferrite. Additionally, the stearic acid helps to delay vulcanization so that it does not occur until intentionally induced during the pressing process. The zinc oxide curatives also help to cure rig the final product.

The resulting sheet is spooled upon a large spool or bobbin with sheets of non-adhesive paper or other light material separating the adjacent layers. As the pigs are calendared 84, a nylon mesh may be applied and embedded into the resulting thin sheet 86. The nylon mesh provides structural support and reinforcement for the thin magnetizable sheet 86.

Sheets of the calendared material may now be unspooled for cutting and punching into usable sizes. After portions have been cut that are easily handled, the resulting sheet is magnetized by using a press incorporating ultra-strong permanent magnets 88. The sheet is placed between the two jaws of the magnetic press in an open brass envelope. The jaws are configured so that a north magnetic pole magnet on one side of the magnetic press faces a south magnetic pole magnet on its counterpart. The pressing process may occur at elevated pressures and temperatures. Magnetizing the sheet 86 at or near the Curie temperature aids in the magnetization process. Particularly, the flexible ferrite sheet may be elevated above the Curie temperature to enhance the magnetization process. Reducing the sheet temperature below the Curie point serves to fix magnetism in the sheet.

The open brass envelope is used so that the resulting magnetized flexible magnetic core sheet will not magnetically adhere to one side or the other of the magnetic press. The brass is generally non-ferromagnetic and serves as a means by which the magnetized sheet can be separated from the magnetic press. The magnetic press may additionally use high pressure in order to better impart its magnetic field and to further cure the flexible magnetic core material as by pressure. Once the magnetization process 88 has taken place, the resulting flexible magnetic core sheet is ready for lamination 90 with the leather upper 52 and the cushioning base 54 material.

As a further element of the method of manufacture of the magnetic insole 50 of the present invention, the perforation process 74 creates a number of stubs or cores that could interfere with the efficient processing. Generally, the punches used to create the perforations are able to eject the core material that has been punched out to create the perforations in the magnetic insole 50. These may be swept away by a whiskbroom or the like in order to keep clear the operating surface of the punch press.

As shown in FIGS. 4–8, a variety of regular and alternating magnetic field configurations may be achieved by using the magnetic press mentioned above with respect to the magnetization 88 of the flexible core material. The jaws of the magnetic press may reflect in mirror image the configurations shown in FIGS. 4–8.

Strontium ferrite is generally able to take on and maintain the magnetization imparted to it by the magnetic press. In so doing, it may form the alternating permanent magnets used in the magnetotherapeutic insole 50 of the present invention. Other strongly magnetic substances that are suitable for use in the present invention may also be used to good advantage, such as barium ferrite.

While the present invention has been described with regards to particular embodiments, it is recognized that additional variations of the present invention may be devised without departing from the inventive concept.

What is claimed is:

1. A method for preparing a flexible magnetic insole for providing magnetotherapy to a foot, the steps comprising:
   providing a laminated sheet, said laminated sheet having a leather upper, a flexible magnetic core coupled to said leather upper, and a cushioning base coupled to said flexible magnetic core;
   said flexible magnetic core including permanent magnetic particles embedded therein with said magnetic particles forming at least one magnetic zone of a first polarity and a plurality of magnetic zones of a second polarity;
   said at least one magnetic zone of first polarity and said plurality of magnetic zones of second polarity being positioned contiguous with one another;
   said at least one magnetic zone of first polarity being contiguous with three of said zones of second polarity, said at least one magnetic zone of first polarity being triangular in shape;
   cutting an insole section from said laminated sheet; and
   perforating said insole section to provide ventilation holes through said insole section.

2. The method for preparing a flexible magnetic insole for providing magnetotherapy to a foot as set forth in claim 1, wherein the step of perforating an insole section further comprises:
   perforating said laminated sheet prior to cutting said insole section to provide a perforated insole section.

3. The method for preparing a flexible magnetic insole for providing magnetotherapy to a foot as set forth in claim 1, wherein the step of providing a laminated sheet further comprises:
   providing a leather sheet, said leather sheet forming said leather upper;
   providing a flexible magnetic sheet, said flexible magnetic sheet forming said flexible magnetic core;
   coupling said flexible magnetic sheet to said leather sheet;
   providing a sheet of cushioning material, said sheet of cushioning material forming said cushioning base; and
   coupling said sheet of cushioning material to said flexible magnetic sheet; whereby
   a three-layer laminated sheet, is provided from which flexible magnetic insoles may be cut.

4. The method for preparing a flexible magnetic insole for providing magnetotherapy to a foot as set forth in claim 3, wherein the step of providing a flexible magnetic sheet further comprises:
   mixing strongly magnetizable, material with an elastic binder to form a mixture;
   rolling said mixture into a sheet; and
   magnetizing said sheet; whereby
   said flexible magnetic sheet is produced in a controllable fashion from a strongly magnetizable material and an elastic binder.

5. The method for preparing a flexible magnetic insole for providing magnetotherapy to a foot as set forth in claim 4, wherein said strongly magnetizable material further comprises:
   powdered or particulate strontium ferrite.

6. The method for preparing a flexible magnetic insole for providing magnetotherapy to a foot as set forth in claim 4, wherein said elastic binder further comprises:
   an elastomer selected from the group comprising neoprene, styrene-butadiene rubber (SBR), and acrylonitrile-butadiene rubber (NBR or nitrile).

7. The method for preparing a flexible magnetic insole for providing magnetotherapy to a foot as set forth in claim 4, wherein said step of mixing strongly magnetizable material with an elastic binder further comprises:
   mixing strongly magnetizable material with an elastic binder, stearic acid, and a mold-release agent.

8. The method for preparing a flexible magnetic insole for providing magnetotherapy to a foot as set forth in claim 7, wherein said step of mixing strongly magnetizable material with an elastic binder further comprises:
   mixing zinc oxide with said strongly magnetizable material, elastic binder, stearic acid, and mold-release agent, said zinc oxide providing cross linking of said elastic binder.

9. The method for preparing a flexible magnetic insole for providing magnetotherapy to a foot as set forth in claim 4, wherein said step of rolling said mixture into a sheet further comprises:
   rolling and pressing said mixture at an elevated temperature to cure said mixture and to provide a magnetizable sheet.

10. The method of preparing a flexible magnetic insole for providing magnetotherapy to a foot as set forth in claim 9, wherein said step of rolling and pressing said mixture further comprises:

providing a nylon mesh; and rolling and pressing said nylon mesh with said mixture; whereby said nylon mesh is incorporated into said magnetizable sheet and provides mechanical support and greater strength to said magnetizable sheet.

11. The method for preparing a flexible magnetic insole for providing magnetotherapy to a foot as set forth in claim 4, wherein said step of magnetizing said sheet further comprises:

providing a magnetizing press having first and second jaws, said first jaw incorporating permanent magnets having a first polarity configuration, said second jaw incorporating permanent magnets having a second polarity configuration, said second polarity configuration being the opposite polarity of said first polarity configuration so that said permanent magnets of said first jaw meet permanent magnets of opposite polarity in said second jaw;

proving a dielectric envelope for fitting between said first and second jaws;

placing at least a portion of said sheet into said dielectric envelope;

placing said dielectric envelope between said first and second jaws;

pressing said dielectric envelope and said sheet between said first and second jaws; and removing said sheet from between said first and second jaws; whereby said sheet is magnetized by said magnetizing press, said sheet more easily removable from said magnetizing press by said dielectric envelope as said dielectric envelope is not attracted to said magnetizing press and as said dielectric envelope provides mechanical support for said sheet and prevents tearing or ripping of said sheet when removed from said magnetizing press.

12. The method for preparing a flexible magnetic insole for providing magnetotherapy to a foot as set forth in claim 11, wherein said dielectric envelope comprises a brass envelope.

13. The method for preparing a flexible magnetic insole for providing magnetotherapy to a foot as set forth in claim 11, wherein said step of pressing said dielectric envelope and said sheet between said first and second jaws further comprises:

heating said sheet above a Curie temperature of said sheet to better magnetize said sheet; and cooling said sheet below said Curie temperature to fix said magnetism in said sheet.

14. The method for preparing a flexible magnetic insole for providing magnetotherapy to a foot as set forth in claim 11, wherein said step of pressing said dielectric envelope and said sheet between said first and second jaws further comprises:

pressing said dielectric and said sheet at an elevated pressure.

15. A method for preparing a flexible magnetic insole for providing magnetotherapy to a foot, the steps comprising:

providing a leather sheet, said leather sheet forming a leather upper;

mixing strongly magnetizable strontium ferrite material with an elastic neoprene binder, stearic acid, a mold-release agent, and zinc oxide to form a magnetizable mixture;

providing nylon mesh;

rolling and pressing said magnetizable mixture with said nylon mesh, said rolling and pressing occurring at an elevated temperature to cure said magnetizable mixture, said nylon mesh providing mechanical support and greater strength to said magnetizable sheet;

providing a magnetizing press having first and second jaws, said first jaw incorporating strongly magnetic permanent magnets having a first polarity configuration, said second jaw incorporating strongly magnetic permanent magnets having a second polarity configuration, said second polarity configuration being the opposite polarity of said first polarity configuration so that said permanent magnets of said first jaw are oppositely opposed said permanent magnets of opposite polarity of said second jaw when said magnetizing press is closed;

providing a dielectric brass envelope for fitting between said first and second jaws;

placing at least a portion of said magnetizable sheet into said dielectric brass envelope, said magnetizable sheet more easily removable from said magnetizing press by said dielectric brass envelope as said dielectric brass envelope is not attracted to said magnetizing press and as said dielectric envelope provides mechanical support for said magnetizable sheet and prevents tearing or ripping of said magnetizable sheet when removed from said magnetizing press;

placing said dielectric brass envelope between said first and second jaws;

closing said magnetizing press;

pressing said dielectric envelope and said magnetizable sheet between said first and second jaws at an elevated pressure, said magnetizable sheet magnetized during said pressing to provide a flexible magnetic sheet;

heating said magnetizable sheet above a Curie temperature of said magnetizable sheet to better magnetize said sheet;

said magnetizable sheet including permanent magnetic particles embedded therein with said magnetic particles forming at least one magnetic zone of a first polarity and a plurality of magnetic zones of a second polarity;

said at least one magnetic zone of first polarity and said plurality of magnetic zones of second polarity being positioned contiguous with one another;

said at least one magnetic zone of first polarity being contiguous with three of said zones of second polarity, said at least one magnetic zone of first polarity being triangular in shape;

cooling said flexible magnetic sheet below said Curie temperature to fix said magnetism in said flexible magnetic sheet;

removing said flexible magnetic sheet from said magnetizing press;

coupling said flexible magnetic sheet to said leather sheet;

providing a sheet of cushioning material, said sheet of cushioning material forming a cushioning base;

coupling said sheet of cushioning material to said flexible magnetic sheet to provide a three-layer laminated sheet from which flexible magnetic insoles may be cut;

cutting an insole section from said laminated sheet; and providing ventilation holes though said insole section.

16. The method for preparing a flexible magnetic insole of claim 15, wherein said first and second polarity configurations of said first and second jaws is selected from the group consisting of:

alternating magnetic triangles, alternating magnetic squares, and series of alternating concentric circles; whereby said magnetizable sheet is magnetized with a magnetic polarity configuration the same as said first and second jaws.

17. A method for preparing a flexible magnetic insole for providing magnetotherapy to a foot, the steps comprising:

providing a leather sheet, said leather sheet forming a leather upper;

mixing strongly magnetizable strontium ferrite material with an elastic neoprene binder, stearic acid, a mold-release agent, and zinc oxide to form a magnetizable mixture;

providing nylon mesh;

rolling and pressing said magnetizable mixture with said nylon mesh, said rolling and pressing occurring at an elevated temperature to cure said magnetizable mixture, said nylon mesh providing mechanical support and greater strength to said magnetizable sheet;

providing a magnetizing press having first and second jaws, said first jaw incorporating strongly magnetic permanent magnets having a first polarity configuration, said second jaw incorporating strongly magnetic permanent magnets having a second polarity configuration, said second polarity configuration being the opposite polarity of said first polarity configuration so that said permanent magnets of said first jaw are oppositely opposed said permanent magnets of opposite polarity of said second jaw when said magnetizing press is closed;

providing a dielectric brass envelope for fitting between said first and second jaws;

placing at least a portion of said magnetizable sheet into said dielectric brass envelope, said magnetizable sheet more easily removable from said magnetizing press by said dielectric brass envelope as said dielectric brass envelope is not attracted to said magnetizing press and as said dielectric envelope provides mechanical support for said magnetizable sheet and prevents tearing or ripping of said magnetizable sheet when removed from said magnetizing press;

placing said dielectric brass envelope between said first and second jaws;

closing said magnetizing press;

pressing said dielectric envelope and said magnetizable sheet between said first and second jaws at an elevated pressure, said magnetizable sheet magnetized during said pressing to provide a flexible magnetic sheet;

heating said magnetizable sheet above a Curie temperature of said magnetizable sheet to better magnetize said sheet;

cooling said flexible magnetic sheet below said Curie temperature to fix said magnetism in said flexible magnetic sheet;

removing said flexible magnetic sheet from said magnetizing press wherein said flexible magnetic sheet includes permanent magnetic particles embedded therein with said magnetic particles forming at least one magnetic zone of a first polarity and a plurality of magnetic zones of a second polarity;

said at least one magnetic zone of first polarity and said plurality of magnetic zones of second polarity being positioned contiguous with one another;

said at least one magnetic zone of first polarity being contiguous with three of said zones of second polarity, said at least one magnetic zone of first polarity being triangular in shape;

coupling said flexible magnetic sheet to said leather sheet;

providing a sheet of cushioning material, said sheet of cushioning material forming a cushioning base;

coupling said sheet of cushioning material to said flexible magnetic sheet to provide a three-layer laminated sheet from which flexible magnetic insoles may be cut;

cutting an insole section from said laminated sheet; and providing ventilation holes through said insole section.

* * * * *